United States Patent [19]

Carter

[11] Patent Number: 5,063,209

[45] Date of Patent: * Nov. 5, 1991

[54] MODULATION OF AIDS VIRUS-RELATED EVENTS BY DOUBLE-STRANDED RNAS

[75] Inventor: William A. Carter, Birchrunville, Pa.

[73] Assignee: HEM Research, Inc., Rockville, Md.

[ * ] Notice: The portion of the term of this patent subsequent to Jan. 2, 2006 has been disclaimed.

[21] Appl. No.: 565,174

[22] Filed: Aug. 10, 1990

Related U.S. Application Data

[63] Continuation of Ser. No. 433,445, Nov. 13, 1989, abandoned, which is a continuation of Ser. No. 124,572, Nov. 24, 1987, abandoned, which is a continuation-in-part of Ser. No. 900,614, Aug. 26, 1986, Pat. No. 4,795,744, which is a continuation-in-part of Ser. No. 886,363, Jul. 17, 1986, abandoned, which is a continuation-in-part of Ser. No. 769,494, Aug. 25, 1985, abandoned.

[51] Int. Cl.$^5$ .................... A61K 31/70; A61K 37/00
[52] U.S. Cl. .................... 514/44; 514/885; 514/889; 514/908; 514/934
[58] Field of Search ................. 514/44, 885, 889, 908, 514/934

[56] References Cited

U.S. PATENT DOCUMENTS

| 3,931,397 | 1/1979 | Harnden | 424/85 |
|---|---|---|---|
| 4,795,744 | 1/1989 | Carter | 514/44 |
| 4,820,696 | 4/1989 | Carter | 514/44 |

OTHER PUBLICATIONS

May 1984 Press Release.
Ampligen Research Program fact sheet, May 1984.
SCRIP Work Pharmaceutical News, Jul. 30, 1984.
SCRIP World Pharmaceutical News, Jun. 3, 1985.
Hahnemann University, "ALUMNI" magazine, fall 1984.
"The Pink Sheet", vol. 46, No. 21, pp. T&G-3,4, May 21, 1984.
UPI report of May 16, 1984.
UPI wire service news reports under various by-lines, May 15 and 16, 1984.
Longo et al., Ann. NY Acd. Sci., 437:421-30.
Spiegel, Serminars in Oncology, 14:1, 1987.
Krigel et al., 1985, Journal of Biological Response Modifiers, 4:358-364.
Friedland et al., monograph TH.4.6 of Jun. 4, 1987, 3rd International Conference on Acquired Immunodeficiency Syndrome (AIDS).
Travers (1984) Nature 311: 410. Zameonik et al., (1978) PNAS 75: 280-4.
Izant et al., (1984) Cell, vol. 36: 1007-16.
Stephanson et al., (1978) PNAS 75: 285-8.

Primary Examiner—Theodore Morris
Assistant Examiner—David M. Brunsman
Attorney, Agent, or Firm—Nixon & Vanderhye

[57] ABSTRACT

The use of mismatched dsRNA, e.g., AMPLIGEN ® for the manufacture of compositions for use in the selective activation of a latent natural defense system within human cells, both cells already infected with AIDS virus as well as cells at risk to infection. Specific treatments for various clinical phase of the biological continuum of AIDS virus-related events ranging from subtle, early immunological lesions to advanced disease are described. Prophylaxis or prevention of AIDS virus related events, such as by introduction of mismatched double-stranded RNA into various blood products or biological fluids to be used in man (e.g., blood transfusion) or around man (e.g., dialysis programs) are also described.

20 Claims, No Drawings

MODULATION OF AIDS VIRUS-RELATED EVENTS BY DOUBLE-STRANDED RNAS

CROSS-REFERENCE TO RELATED APPLICATIONS

This is a continuation of application Ser. No. 07/433,445, filed Nov. 13, 1989, now abandoned, which is a continuation of application Ser. No. 07/124,572, filed Nov. 24, 1987, now abandoned, which is a continuation-in-part of application Ser. No. 900,614 filed Aug. 26, 1986 now U.S. Pat. No. 4,795,744, which in turn, is a continuation-in-part of application Ser. No. 886,363 filed July 17, 1986 now abandoned, which in turn, is a continuation-in-part of application Ser. No. 769,494 filed Aug. 25, 1985, now abandoned.

AIDS (Acquired Immunodeficiency Disease Syndrome) represents a major public health threat of the Twentieth Century. Because of its biologically variable nature, its subtle means of spread from individual to individual, and its "latent" disease period which defies even the ready detection of its very presence, AIDS has rapidly evolved into an epidemiologic dilemma of unprecedented proportions. Indeed, even with the considerable resources already deployed to increase diagnostic capabilities, the available technologies still fall well short of the necessary requirements to gain firm control of this problem within any section of the population (e.g., see Proceedings of Workshop entitled "Experience with HTLV-III Antibody Testing, an Update on Screening, Laboratory and Epidemiological Correlations", sponsored by the Center for Drugs and Biologics, FDA, National Institutes of Health, and Centers for Disease Control, held on July 31, 1985, at the National Institute of Health, Bethesda, Md.; see also, Budiansky, S. in *Nature*, volume 316, page 96, July 11, 1985). Two different designations for the AIDS virus exist; LAV is the designator for the AIDS virus isolated at the Pasteur Institute, Paris, France and HTLV-III is the designator for the AIDS virus isolated at the National Institute of Health, Bethesda, Md., U.S.A. Frequently in this text, the AIDS virus will be referred to generically or designated HTLV III or LAV without intending to differentiate between them. Furthermore, the term "AIDS virus" in the specification includes any and all other viruses which may be associated with producing AIDS, whether yet isolated or not.

Current therapeutic considerations have taken one of two approaches: immunological (vaccine production) or direct attacks on the virus itself (antiviral therapy). While vaccine production initially appeared extremely promising, at least in theory, new knowledge of the viral composition has significantly undermined this promise; namely, the virus apparently readily mutates or changes its basic biochemical structure such that critical viral antigenic "determinants"—necessary for vaccines to be effective—readily undergo mutation or change. For example, HTLV-III isolates in California, Maryland and England have recently been found to be significantly different from each other when their genomic content(s) has been rigorously analyzed. The implication of such studies is that vaccination against AIDS will not have widespread lasting benefits such as the conclusively beneficial/durable results historically characteristic of most other vaccines, such as those directed against polio virus, measles virus, etc.

In the second, or direct antiviral approach, other scientists have tested several compounds including HPA-23, suramin, ribavirin, interferon and fascarnet, etc. These compounds have been introduced into either the laboratory or clinical studies with little-to-no evidence of therapeutic success to date. Indeed, consistent evidence of high toxicity and/or severe side-effects has been reported in nearly every instance (e.g., see summary prepared by M. Clark, *Newsweek*, page 71, Aug. 5, 1985; also, C. Wallis, *Time*, pages 40–47, Aug. 12, 1985). None of these drugs are indeed new or able to be selectively directed against the underlying disorder; namely, multiplication of AIDS virus in certain cells. For example, HPA-23 is a combination of heavy metals (reminiscent of the use of arsenic to treat venereal diseases in the 1920s, or pre-penicillin era); suramin is actually an antiparasitic (sleeping sickness) compound and fascarnet is an anti-herpes virus compound. The latter two compounds may inhibit an AIDS-virus related enzyme termed "reverse transcriptase", but there is no evidence that such an enzymatic inhibition, in fact, would result in any therapeutic improvement or disease prevention/amelioration. Similarly, interferon, which is as toxic and non-specific as the above-mentioned compounds, may have some limited activity on AIDS-virus related tumors, but numerous studies indicate that it holds little promise as an effective antiviral against AIDS virus, or most other viruses for that matter.

Mismatched double-stranded RNA is a known form of macromolecular RNA (see U.S. Pat. Nos. 4,024,222 and 4,130,641) in which destabilization of the double helix prevents base pairing. Mismatched dsRNA is well known for its interferon-induction properties which indicate a mechanism unrelated to interferon induction per se (e.g., see European Patent Application 83305426.5 filed Aug. 15, 1983, entitled "Antiproliferative Action of dsRNAs on Tumor Cells"). A typical therapeutic embodiment of mismatched double-stranded RNA is the synthetic dsRNA formed by complexes of polyriboinosinic and polyribocytidylic/uridylic acid, such as $rI_n \cdot r(C_x,U \text{ or } G)_n$ where x has a value from 4 to 29, e.g. $rI_n \cdot r(C_{12}U)_n$ herein referred to as "Ampligen", a trademark of HEM Research, Inc., of Rockville, Md., U.S.A. Many mismatched dsRNA polymers which behave similarly to Ampligen have been studied. The key therapeutic advantage of mismatched dsRNAs over other forms of natural and/or synthetic dsRNAs is their reduced toxicity in animals and man. For example, Lampson et al in U.S. Pat. No. 3,666,646 described earlier complexes of dsRNA which are capable of triggering various interferon-related effects, but the toxicity of such compounds precluded any clinical utility in the treatment of cancer or related disorders.

The inventor has fully described the known activities of various interferons, interferon inducers and dsRNAs in his recent textbooks on the subject (e.g., see the inventor's chapter in *Anticancer and Interferon Agents*, pages 301 through 319, edited by R. M. Ottenbrite and G. B. Butler, Marcell Dekker, New York, 1984; also see *Handbook of Experimental Pharmacology on Interferons*, edited by P. E. Come and W. A. Carter, 1984, published by Springer-Verlag, New York and Heidelberg; pages 535–555 fully describe the known properties of dsRNAs).

Mismatched dsRNA, e.g., Ampligen, is now known to have therapeutic activity against certain human tumors, particularly kidney cancer. Although currently thought of as purely an "interferon inducer", dsRNAs are active on certain human tumors which are completely resistant to interferon itself as fully described in European Patent Application 83305426.5 of which the present applicant is an inventor.

Similar to the lack of activity against certain tumors, it has now been demonstrated that virtually all types of interferon exhibit no significant activity in the treatment of the AIDS virus. Being known "interferon inducers", it is particularly surprising that mismatched dsRNAs have application in the treatment of AIDS-related disorders.

The present invention is based on another new and unexpected property of dsRNA, especially mismatched dsRNA, as exemplified by Ampligen, which has a surprisingly wide range of applicability to the treatment of AIDS-related disorders.

The present invention provides the use of a dsRNA in the manufacture of a composition for use in the treatment of AIDS by therapy or prophylaxis.

This invention includes a method of treating retrovirus or T-cell lymphotropic virus-induced conditions, including AIDS, in a person infected with same, by administering to that person an amount of dsRNA sufficient to therapeutically benefit AIDS-related disorders. A second virus inhibitor, such as interferon, may be concurrently administered to the patient.

An important symptom of AIDS is the suppression of the normal immune state as indicated by the immune skin response. This is restored during successful treatment with dsRNA.

Accordingly, the invention includes the use of dsRNA in the manufacture of a medicament for restoring an anergic immune state to a substantially normal immune state as measured by testing the immune skin response.

The dsRNA may be a mismatched dsRNA.

HTLV III/LAV infection produces a particularly wide range of severity of response from relatively asymptomatic carriers to profound immunological paralysis. To treat this range of response, a wide range of dosage of dsRNA may be appropriate. When low dosages are employed, the use of non-mismatched dsRNA may be appropriate and dosages may be sufficiently low to avoid the adverse reactions mentioned above. Where higher doses are appropriate the need to use mismatched dsRNA will be greater.

Preferably, the dsRNA is such as to produce an elevated intracellular concentration of 2'-5'A oligomers without host toxicity, e.g. due to an accelerated bioavailability, a structure adapted to activate 2'-5'A oligomer production without producing side effects, or due to a relatively short half life following administration.

By "matched dsRNA" are meant those in which hydrogen bonding (base stacking) between the counterpart strands is relatively intact, i.e. is interrupted on average less than one base pair in every 29 consecutive base residues. The term "mis-matched dsRNA" should be understood accordingly.

The dsRNA may be a complex of a polyinosinate and a polycytidylate containing a proportion of uracil bases or guanidine bases, e.g. from 1 in 5 to 1 in 30 such bases (poly I. poly (C4–29×U or G).

The dsRNA may be of the general formula $rI_n.C(C_{12}U)_n$. Other suitable examples of dsRNA are discussed below.

The composition may comprise the dsRNA and an AIDS inhibition assisting agent, such as a lymphokine, e.g. an interferon or an interleukin such as IL-2.

The invention accordingly includes the use of dsRNA in the manufacture of a pharmaceutical composition for the prevention or treatment of AIDS in a person comprising, in combination, a dsRNA and a lymphokine such as an interferon.

Preferably the composition contains the dsRNA and the interferon in the ratio of 0.01 to 1000 micrograms of dsRNA to 0.1 to 100,000 IRU of interferon.

The invention further includes a method of rendering a, preferably human-originating, biological fluid or, preferably human-originating, cells resistant to viral infection, enhancing the resistance thereof, or mitigating the effects of infection therefrom comprising admixing or contacting said biological fluid or cells with an AIDS-inhibiting amount of a dsRNA.

The biological fluid may be human blood or a fraction thereof for instance for use in transfusion or dialysis.

The invention further includes as a composition of matter, human blood or a fraction thereof or human cells and an AIDS-inhibiting amount of a mismatched dsRNA.

Furthermore, the invention includes also a process of removing or inactivating AIDS viruses from a device for handling parenteral fluids or mitigating the effect of infection therefrom comprising contacting said device with a composition containing an AIDS-inhibiting amount of a dsRNA.

The invention includes also a composition for use in the treatment of AIDS comprising a dsRNA and a pharmaceutically acceptable carrier or diluent together with instructions for use in the treatment of AIDS.

Thus there are disclosed hereinafter by way of example, therapeutic methods of selectively inhibiting human viruses, specifically the AIDS virus, without significant toxicity to normal cells; methods of inhibiting, delaying or preventing a person from becoming infected with AIDS virus; methods of preventing or treating AIDS-related disorders in humans; methods of treating human biological fluids, cells and tissue products to prevent or arrest infection or contamination with AIDS virus; and methods of correcting specific lesions associated with AIDS virus, including loss of interferon receptors on cells within the immune system, cutailment or reduction of intracellular 2'-5'A synthetase and the reduction or loss of intracellular dsRNAs in selected cells of the immune system. Pharmaceutical compositions for use in these methods are also disclosed.

The use of dsRNA is adapted to correct specific lesions associated with AIDS virus, including loss of interferon receptors on various critical cells within the immune system, curtailment/reduction of intracellular 2'-5'A synthetase in various critical cells within the immune/bodily defense system, and reduction or loss of intracellular dsRNA in various critical cells within the immune/bodily defense system.

The mismatched dsRNAs preferred for use in the present invention are based on copolynucleotides selected from poly ($C_n,U$) and poly ($C_n,G$) in which n is an integer having a value of from 4 to 29 and are mismatched analogs of complexes of polyriboinosinic and polyribocytidilic acids, formed by modifying $rI_n.rC_n$ to incorporate unpaired bases (uracyl or guanine) along the polyribocytidylate ($rC_n$) strand. Alternatively, the dsRNA may be derived from poly (I). poly (C) dsRNA by modifying the ribosyl backbone of polyriboinosinic acid ($rI_n$) e.g. by including 2'-O-methyl ribosyl residues. These mismatched analogs of $rI_n.rC_n$, preferred ones of which are of the general formula $rI_n.r(C_{12},U)_n$, are described by Carter and Ts'o in U.S. Pat. Nos. 4,130,641 and 4,024,222 the disclosures of which are hereby incorporated by reference. The dsRNA's described therein generally are suitable for use according to the present invention.

Other examples of mismatched dsRNA for use in the invention include:

poly (I). poly ($C_4$, U)
poly (I). poly ($C_7$, U)
poly (I). poly ($C_{13}$, U)
poly (I). poly ($C_{22}$, U)
poly (I). poly ($C_{20}$, G)
poly (I). poly ($C_{29}$, G) and
poly (I). poly ($C_p$) 23 G>p Pharmaceutical compositions in accordance with this invention include the mismatched dsRNA, optionally also an interferon, together with a pharmaceutically acceptable carrier or diluent. Pharmaceutical compositions contemplated by this invention include those adapted for parenteral administration in a suitable pharmaceutical vehicle.

Thus, for example, parenteral solutions, suspensions and dispersions can be prepared as required according to known pharmaceutical techniques with sterile or pyrogen-free water as the solvent/diluent optionally also with physiologically acceptable salts.

It will be understood that the absolute quantity of active ingredients present in any dosage unit should not exceed that appropriate to the rate and manner of administration to be employed, but on the other hand should also desirably be adequate to allow the desired rate of administration to be achieved by a small number of doses. The rate of administration will moreover depend on the precise pharmacological action desired.

The amount of mismatched dsRNA administered is preferably sufficient to achieve a level of from 0.01 micrograms per milliliter of body fluid after equilibration of the dsRNA level through the body fluid up to 1000 micrograms per milliliter in the systemic circulation immediately following administration. When concurrently administered, interferon is preferably included in an amount that results in a level of 0.1 to 100,000 IRU per milliliter of body fluid. Generally, the amount to be administered will depend on the severity of the condition, in particular the level of available intracellular bioactive dsRNA, 2'-5' oligo A molecules or 2'-5'A synthetase. As used herein, the term body fluid is the solution of serum, vitamins, etc. which circulates within the organism and bathes the tissues. Expected body fluid volumes of patients are of course known to practitioners and are published as charts and tables, which are routinely available.

As indicated above, the invention includes the treatment of biological fluids with dsRNA and similarly the treatment of cells with dsRNA. Blood products such as whole blood used in transfusions or components of whole blood, such as "packed (concentrated) red blood cells, packed white blood cells, platelet concentrates or serum protein fractions such as immunoglobulins" may be treated in this way. Such blood products may have mismatched dsRNA at appropriate concentrations added to them at the time of initial isolation and prior to any cryopreservation.

Alternatively, an effective concentration may be added to the blood product immediately prior to injection into the recipient. In such cases, the operator may simply refer to a standard table of body fluid volumes which interrelate the weight of the recipient to his or her body fluid volume, which is the total of the body fluid volume of the patient and the body fluid volume available for equilibration with the necessary quantity of the dsRNA. A sixty to seventy kilogram patient will have a body fluid volume of approximately five to six liters.

Blood products as described above may have undetected retroviruses, especially AIDS-related virus associated with them. The objective is to provide a final concentration in the blood product in question which prevents the "seeding" of the occult retroviruses in the diverse tissues of the recipient of the blood product. By preventing a successful seeding of such retrovirus one can prevent what otherwise would become a life threatening viral proliferation when the contaminated transfused cells and/or cell products are admixed and/or distributed throughout the recipient's system.

Other important uses for this technique are instances where the patient's blood is transitorily exposed to donor blood and/or blood products, such as through a membrane which may be defective or may serve to transmit retroviruses, examples of such instances include the use of equipment such as extracorporeal pumps and associated devices used during cardiac surgery, cardiac bypass surgery, organ transplants and so forth. This differs from the situation in which whole blood or blood products are infused into the patient. Transitory exposure through a membrane involves only temporary exposure to possibly contaminated blood, exposure lasting as little as a few minutes or for as long as several hours depending on the length of the surgical or other medical procedure. Similar exposure is possible with renal dialysis equipment in which the presence of an effective concentration of dsRNA will thwart the possibility that undetected retroviruses may traverse membranes and seed the body of an individual connected to such equipment.

Medical literature also documents the passage of the AIDS-related virus through nasal and lachrynal secretion. Medical equipment and devices having the potential to transfer retroviruses from one patient to another are also effectively treated with mismatched dsRNAs according to the invention. Illustrative examples include inhalation and inhalation therapy equipment used to assist in respiration as well as instruments used to examine and treat eyes.

Aerosols containing dsRNAs may be sprayed onto the contacted portions of the device to prevent contamination of equipment due to multiple users.

The amount of dsRNA included in or added to whole blood or blood products will depend on the overall dilution rate of the blood or blood products in use. First, the tissue volume of the patient may be determined based upon the size of the patient, then the quantity of dsRNA may be calculated. A transfused blood product will require a greater concentration of the dsRNA because of the extensive overall dilution as compared with an extracorporeal blood pump or dialysis equipment using a membrane in which the donor patient is to be protected without concern for dilution to immobilise any retrovirus in the donated material. Preferred amounts for non-diluted uses are in the range of from about 0.1 microgram to about 200 micrograms per milliliter of body fluid. In contrast, for whole blood, usually available in containers or 350 and 500 ml, a sixty kilogram patient with a whole body fluid volume of between about five and six liters will require about 200 mg of dsRNA to achieve a concentration of 40 micrograms per milliliter upon equilibration.

The invention will be illustrated by the following description of examples of the use of dsRNA.

Mismatched dsRNAs, e.g., Ampligen, were formulated in aqueous solution such that, when added to various human cells, transient concentrations of 0.01 microgram to 250 microgram per milliliter of fluid (bathing cells) was obtained. A variety of different cells, all potential targets for infection with HTLV-III (AIDS virus), were used.

Below described is a typical experiment with H-9 cells, a human lymphoid cell which can be acutely or chronically infected with HTLV. The cells were grown under standard conditions (e.g., see Mitsuya et al, *Science* volume 226, page 172, 1984) and analyzed for several weeks with respect to the presence of HTLV enzymes or HTLV-specific proteins. Various concentrations of Ampligen were added, before, after or simultaneously with the virus to thus mimic various clinical conditions. Most importantly, careful analyses of cell number, morphology, etc., were done to determine if the mismatched dsRNA had various non specific effects on lymphoid cell growth as had been described by Mitsuya with other inhibitors. Cells, at different times during the experiment, were isolated and studied by HPLC analysis of the 2',5'-A oligomers using methods described by Lee et al (*Biochemistry*, volume 24, page 551, 1985). Certain A oligomers, when present in nature, are known to confer viral resistance to cells, but it has not been previously described, or anticipated, that a test compound (synthesized by man) could precisely trigger this natural reaction selectively, and thus strengthen a natural defense mechanism against viruses in general, and AIDS virus in particular.

TABLE 1

Effect of Ampligen on HTLV-III Infectivity

| Day | % HTLV Positive Cells | | Reverse Transcriptase | |
| --- | --- | --- | --- | --- |
|  | + Drug | − Drug | + Drug | − Drug |
| Experiment A | | | | |
| 4 | 0 | 50 | 1,412 | 24,287 |
| 9 | 7 | 90 | 144,632 | 1,243,300 |
| Experiment B | | | | |
| 3 | 0 | 0 | 353 | 323 |
| 7 | 0 | 0 | 400 | 1,200 |
| 10 | 0 | 5 | 800 | 2,261 |
| 14 | 2 | >80 | 1,100 | 112,247 |
| 17 | 5 | >90 | 1,200 | 1,560,000 |

Experiment A was conducted with 25 times more virus (expressed as infectious units) than target cells whereas Experiment B was conducted with 10 times more cells (designated H-9 cells) than virus. Percent cells positive refers to cells which expressed HTLV-III markers designated p24 and p19 as determined by immunofluorescence; reverse transcriptase refers to a viral enzyme measured in the cell supernatant by the standard template designated poly rA/dT. Concurrently, cell counts were done: the cells multiplied at normal growth rates at all concentrations of Ampligen tested (up to 300 micrograms per milliliter). In experiments A and B, Ampligen (50 micrograms per milliliter) was added on day 1. HPLC analysis showed (by day 3–7 in either Experiment A or B) a specific shift in the 2',5'-oligomer profile such that the higher (less antiviral) molecular weight (MW) oligomers shifted to the lower (most antiviral) MW oligomers which contributed to a selective and strong suppression of the AIDS virus.

Similar experiments were conducted with various other human cells which are potential in vivo targets for AIDS virus: These experiments included other cells functionally determined to be NK (natural killer) cells, T helper cells, T suppressor cells and mononuclear cells, etc. In all instances, various concentrations of mismatched dsRNA were able to selectively arrest and/or prevent HTLV multiplication without any effect on normal cell growth and maturation. Proliferation of the T cells in culture was maintained by the standard addition of IL-2 factor as well known to those familiar in the art of cell biology. The selective suppression of HTLV by mismatched dsRNA was consistently associated with a specific shift, or enhancement, in the 2',5'-oligomer profile as determined by HPLC analysis.

COMPARISONS OF MISMATCHED dsRNAs WITH INTERFERON

Since dsRNAs, being "interferon inducers", might be viewed as simply working through (via) an interferon mechanism, any activity of interferon per se might be thought to suggest activity by dsRNA. Thus, the following experiments establish that uniqueness of the present invention by demonstrating no significant activity of interferons of virtually all types in the face of very potent and specific anti-AIDS virus activity by Ampligen.

CEM (another human T cell line) cells were treated with either 250 I.U./ml recombinant alpha interferon, 250 I.U./ml natural beta interferon, 50 I.U./ml natural gamma interferon of 50 μg/ml Ampligen for 18 hours prior to infection with LAV. After 15 days of culture, the following data were collected.

TABLE 2

Effect of Ampligen on LAV Infectivity

|  | Reverse transcriptase [cpm/ml culture fluid] | indirect immunofluorescence [% of cells with LAV antibody binding] |
| --- | --- | --- |
| untreated | 1,147,000 | 49% |
| alpha interferon | 503,000 | 5% |
| beta interferon | 1,500,000 | 60% |
| gamma interferon | 360,000 | 30% |
| Ampligen | 24,000 | <1% |

The data indicate a profound inhibition of viral replication by Ampligen.

Thus, dsRNA (Ampligen) inhibits (>99%) HTLV-III/LAV infection in H9 (T4) cells and CEM (T4) cells. Interferons alpha, beta and gamma are marginally active or inactive. Viral inhibition by Ampligen is very selective and occurs without any measurable effect on cell growth.

Thus, Ampligen inhibits HTLV-III/LAV virus replication by a mechanism distinct from interferon. This finding suggests that Ampligen and interferon or other drugs could be used in combination, whereby Ampligen would inhibit viral replication and the interferon could be used in stimulating the immune system to restore pre-disease function.

In the restoration of the natural antiviral state Ampligen acts distal to the AIDS/ARC block in the antiviral pathway to restore a natural antiviral RNase activity which destroys the viral genome.

Therefore, the drug has the potential to inhibit viral replication, as well as to augment the immune response. Thus, it should be noted that Ampligen is not simply a reverse transcriptase inhibitor of the virus, but acts through the dual mechanisms of human immune system stimulation and establishment of an antiviral state in target cells. Ampligen is readily set apart from interferons, in that it may well be able to cure viral infections and viral induced tumors in animals which are completely refractory to exogenous interferon therapy. These observations distinguish Ampligen from many other drugs proposed for use against this disease.

In related studies, the pathophysiology of AIDS was studied and unexpected and previously undetected biochemical lesions in individuals predisposed (homosexual) to AIDS were detected. Such lesions are correctable by Ampligen and explain its potent antiviral activity in the face of nominal activity (if any), by interferons or most other compounds which have been tested.

First, it was observed that the missing critical biochemical co-factor was dsRNA, in the T lymphocytes of each of 6 individuals predisposed to AIDS (homosexual males) and in each of 6 AIDS victims. Measurements were made of dsRNAs by standard techniques following cell disruption. The effect of Ampligen can thus be accurately viewed as specific replacement therapy for a critical biochemical entity needed for humans to withstand virus attack at the subcellular level. When dsRNA is present naturally or added, as via Ampligen therapy, an active RNase L is formed which then "eats-up" (hydrolizes), or destroys, the viral mRNA thus stopping or containing the viral infection. Subsequently to the filing of the USA priority application, Preeble et al reached a complementary conclusion (September 1985 issue of *Journal of Infectious Diseases*, pages 457–465, entitled "Interferon Induced 2'-5' Oligoadenylate Synthetase During Interferon Alpha Therapy in Homosexual Men with Kaposi's Sarcoma: Marked Deficiency in Biochemical Response to Interferon in Patients with Acquired Immunodeficiency Syndrome"). They showed that the addition of interferon to immune cells from AIDS victims did not result in the expected boost in this specific intracellular pathway, a first line of defense against various viruses.

Second, it was determined that AIDS virus infection itself caused a further loss, or alteration, in the interferon receptor on the cell surface such that interferon could not bind well and could not therefore inititiate the critical "cascade" of biochemical events normally leading to arrest of viral infection and restoration/maintenance of immune competence. It was further observed that unusually low levels of 2'-5'A synthetase follow HTLV-III infection. Thus, AIDS virus infection itself is characterized by applicant at least three (3) deleterious events which however, can be specifically remedied by Ampligen or dsRNA therapy: (1) loss of interferon receptors, (2) reduction in 2'-5'A synthetase, and (3) abnormally low intracellular dsRNA.

In the relevant biochemical pathway, dsRNA works downstream or distal to the biochemical lesions in individuals at risk (with or without active AIDS virus infection), thus restoring normal antiviral response capability.

dsRNA is very efficiently taken up by cells and therefore does not require an intact IFN receptor. Further, mismatched dsRNA is also available as bioactive fragments to accelerate intracellular uptake and distribution. Thus, dsRNA has the potential to readily cross the blood-brain barrier, which may be a residual reservoir of AIDS virus in some individuals.

Typically, dsRNA for use in the present invention will be of the molecular size exemplified in U.S. Pat. Nos. 4,024,222 and 4,130,641 but much lower molecular weight dsRNA, obtainable as fragments of the parent molecule are also effective. These may for instance be of one half to one tenth the size of the typical dsRNA materials described previously.

dsRNA activates the 2'-5'A polymerases and promotes the synthesis of a 500-fold increment in the active antiviral oligonuleotides over that possible with interferons alone (dsRNA leads to 250 nanomoles of 2'-5' oligo A in $1.6 \times 10^8$ cells whereas 200 units/ml IFN lead to only 0.5 nanomoles of 2'-5' oligo A.

Similar phenomena were observed by applicant in the NK cells of individuals at risk to development of AIDS, or possessing frank AIDS. A similar situation exists with respect to the levels of Natural Killer cell (NK) activity in AIDS/ARC patients. However, much less is known regarding the mechanisms of NK regulation.

AIDS/ARC patients and healthy members of "at-risk" groups often have weak immunosurveillance capacity (functional NK and T lymphocytes) and cannot be re-activated by interferons. Ampligen acts distal to the disease block and can activate cytotoxic lymphocytes.

The above theories have been tested clinically in the following confidential trial.

A 60 kg adult male with an AIDS-related complex of intermediate severity (lymph nodes enlarged and unable to eat solid foods for almost one year due to enlarged lymph nodes, AIDS-virus concentration greater than $10^5$ particles per ml of blood but having no evidence of tumors or other infections) was treated with 200 mg mismatched dsRNA (Ampligen) admixed with physiologic saline solution by intravenous drip over a period of 30 minutes. This infusion resulted in a concentration of approximately 40 mcg (0.04 mg) per ml of body fluid when the dsRNA was completely circulated throughout the body and fully equilibrated with all of the extracellular body fluid. The dsRNA was infused into the patient on 6 consecutive treatment intervals spaced 2-3 days apart and was sufficient to rid the patient's body of all measurable AIDS-related virus and to correct the patient's deteriorated immune function. Restoration of the immune function was indicated by a 50% improvement in the ratio of T4/T8 lymphocytes, a ratio recognized as a reliable measurement of general immune capability with respect to retroviruses. Further, at the conclusion of therapy the patient's immune capability, as measured by skin testing, returned to normal from the anergic condition that was measured prior to administration of the mismatched dsRNA. The patient was able to resume eating solid food at the conclusion of therapy and his conditions continues to progress.

Therapeutic combinations of mismatched dsRNAs and lymphokines exhibit enhanced effectiveness in inhibiting viral (HIV) replication.

Table 3 shows the synergistic activity of dsRNA and lymphokines on viral replication. A retrovirus (HIV) was exposed to graded doses of recombinant beta interferon without or with dsRNA. Normally, the viral infection caused extensive cytolysis but dsRNA at very low doses (12.5 micrograms/ml) causes substantial residual protection even after 5 days of viral replication and also had a pronounced and unexpected enhancing effect on the activity of interferon. Similar experiments summarized in Table 4 demonstrate the ubiquity of the effect both with respect to other immune system components (cells) and other lymphokines.

Lymphokines of particular interest include the interferons, as discussed above, both naturally occurring and made recombinant technology. Also the interleukins, specifically interleukin-2 (IL-2) and recombinant interleukin-2 (rIL-2), and tumor necrosis factor (TNF) may be considered. Also included are lymphokine activated killer cells (LAK) formed in animals in response to exposure to a lymphokine.

When interferon (alpha) is used as the lymphokine, an amount of from 0,01 to 100,000 IRU per milliliter of the patient's body fluid is provided. When IL-2, preferably rIL-2, is the lymphokine, the amount administered lies within a range of about $10^2$ IL-2 units per kg of the patient's body weight up to a value approaching unacceptable levels of toxicity in that patient, which may be as high as $10^6$ IL-2 units. However, most effective, toxic-reaction manageable values are in the range of from about $10^3$ to about $10^4$ IL-2 per kg of body weight.

TABLE 3

Anti-HIV Activity of Combined rIFN-β and Ampligen Treatment in T-Cell Cultures

| rIFN-β (Units/ml) | Percent Protection* | | | |
|---|---|---|---|---|
| | 4 Day | | 5 Day | |
| | −Ampl | +Ampl± | −Ampl | +Ampl |
| 1250 | 58 | 100 | 19 | 64 |
| 625 | 42 | 100 | 8 | 55 |
| 312 | 31 | 94 | 4 | 44 |
| 156 | 31 | 90 | 2 | 44 |
| 78 | 8 | 57 | 2 | 25 |
| 39 | 5 | 46 | 0 | 17 |
| 19.5 | 2 | 24 | 0 | 11 |
| 9.7 | 0 | 22 | 0 | 5 |

*Average values, n = 3. Standard deviation were always within 10% of values.
Cells were incubated in the presence or absence of rIFN-β (Triton Biosciences, Inc.) and Ampligen for 4 hours prior to virus challenge. Effectors were assayed in 96-well microtiter plates using MT2 as target cells and HTLV-IIIB as virus at an M.O.I. of 0.1–1.0.
±Ampligen = 12.5 μg/ml. Percent protection provided by Ampligen alone: 4 day, 31%; 5 day, 3%.

TABLE 4

Inhibition of HIV Replication by rIFN-αA and rIFN-β ser 17 with and without Ampligen

| Effector* | cpmRT/ml ($\times 10^{-3}$) | Avg. cmpRT/ml ($\times 10^{-3}$) | % Decrease |
|---|---|---|---|
| Control-1 | 877 | 910 | — |
| Control-2 | 943 | | |
| Ampligen-1 | 896 | 852 | 6 |
| Ampligen-2 | 807 | | |
| rIFNαA-1 | 426 | 428 | 53 |
| rIFNαA-2 | 430 | | |
| rIFNβ-1 | 396 | 398 | 56 |
| rIFNβ-2 | 400 | | |
| Ampligen + rIFNαA-1 | 41 | 47 | 95 |
| Ampligen + rIFNαA-2 | 54 | | |
| Ampligen + rIFNβ-1 | 41 | 44 | 96 |
| Ampligen + rIFNβ-2 | 48 | | |

*Equal density cultures of H9/HTLV-IIIB were incubated in duplicate in the presence and absence of effectors. Conditioned culture fluids were harvested after 48 hours and assayed for reverse transcriptase activity. No inhibition of cell division was observed.
IFNs = 500 μ/ml
Ampligen = 50 μg/ml The combination of a dsRNA and a lymphokine, administered separately, including prior administration of the lymphokine to "prime" the relevant cells, or concurrently, protects cells of the immune system from viral infection. The degree of protection conferred by the combination is greater than that conferred by the dsRNA alone. Importantly, the combination of agents causes no deleterious inhibition of the normal cell division process.

AMPLIGEN ® is a registered trademark of HEM Research, Inc., USA.

What is claimed:

1. A method of treating retrovirus or T-cell lymphotropic virus-induced conditions including AIDS in a person infected with same comprising administering to that person an amount of dsRNA sufficient to therapeutically benefit AIDS-related disorders.

2. The method of claim 1 in which the dsRNA is mismatched dsRNA.

3. The method of claim 2 in which the dsRNA is a complex of a polyinosinate and a polycytidylate containing of from 1 in 5 to 1 in 30 uracil or guanidine bases.

4. The method of claim 3 in which the mismatched dsRNA is $rI_n \cdot (C_{12}U)_n$.

5. The method of claim 1 in which the dsRNA is administered in an amount sufficient to result in a level of 0.01 to 1000 microgram per milliliter of the patient's body fluid.

6. The method of claim 1 in which an AIDS inhibitor is administered concurrently with the dsRNA.

7. The method of claim 1 in which a second AIDS virus inhibitor is concurrently administered to the patient together with the dsRNA.

8. The method of claim 1 in which a lymphokine is administered with the dsRNA as an AIDS inhibition assisting agent.

9. A method of treating AIDS in a person infected with same comprising administering to that person, in combination, an amount of mismatched dsRNA sufficient to benefit AIDS-related disorders and an interferon or an interleukin in an amount sufficient to assist in inhibiting AIDS.

10. The method of claim 9 in which the mismatched dsRNA and the interferon are administered in an amount sufficient to result in a ratio of 0.01 to 1000 microgram per milliliter of dsRNA to 0.1 to 100,000 IRU of interferon in the patient's body fluid.

11. A therapeutic composition for the prevention and treatment of retrovirus or T-cell lymphotropic virus including AIDS in a person comprising, in combination, a viral-inhibiting amount of dsRNA in combination with an AIDS-inhibiting amount of interferon, the dsRNA present in an amount when administered to a person to result in a level of 0.01 to 1000 micrograms per milliliter of body fluid and the interferon present in an amount when administered to a person to result in a level of 0.1 to 100,000 IRU per milliliter of body fluid.

12. The therapeutic composition of claim 11, in which the dsRNA is mismatched dsRNA.

13. The therapeutic composition of claim 11 in which the mismatched dsRNA is $rI_n \cdot (C_{12}U)_n$.

14. A method of rendering a human-originating biological fluid or cells resistant to infection with retrovirus or T-cell lymphotripic virus including AIDS virus, enhancing the resistance thereof, or mitigating the effect of infection therefrom comprising admixing or contacting said biological fluid or cells with a virus-inhibiting amount of dsRNA.

15. The method of claim 14 in which the dsRNA is mismatched dsRNA.

16. The method of claim 14 in which the mismatched dsRNA is $rI_n \cdot (C_{12}U)_n$.

17. The method of claim 13 in which the biological fluid is human blood or a fraction thereof, or the cells are NK cells, T-cells, T-suppressor cells, T-helper cells, spermatozoa, ova or fetal cells.

18. As a composition of matter, human blood or a fraction thereof or human cells and an effective amount of a mismatched dsRNA.

19. A process of removing or inactivating retroviruses or T-cell lymphotropic viruses including AIDS viruses from a device for handling parentheral fluids or mitigating the effect of infection therefrom comprising contracting said device with a composition containing an AIDS-inhibiting amount of a dsRNA.

20. A method of restoring an anergic immune state to a substantially normal immune state, as measured by skin testing, said method comprising administering to a person having an anergic immune state an effective amount of dsRNA.

* * * * *